United States Patent [19]

Van Doorn et al.

[11] Patent Number: 5,350,725

[45] Date of Patent: Sep. 27, 1994

[54] POLYMERIZATION PROCESS

[75] Inventors: Johannes A. Van Doorn; Harry van der Heijden; Hans A. Stil, all of Amsterdam, Netherlands

[73] Assignee: Shell Oil Company, Houston, Tex.

[21] Appl. No.: 72,209

[22] Filed: Jun. 4, 1993

Related U.S. Application Data

[62] Division of Ser. No. 934,224, Aug. 25, 1992, Pat. No. 5,247,065.

[30] Foreign Application Priority Data

Aug. 30, 1991 [NL] Netherlands ............... 9101465

[51] Int. Cl.$^5$ .............................................. B01J 31/24
[52] U.S. Cl. .................................. 502/162; 502/168; 502/170
[58] Field of Search ..................... 502/162, 168, 170

[56] References Cited

U.S. PATENT DOCUMENTS

| | | |
|---|---|---|
| 4,851,379 | 7/1989 | Van Broekhoven et al. ...... 502/162 |
| 4,877,861 | 10/1989 | Van Doorn et al. ............... 528/392 |
| 5,026,674 | 6/1991 | Brown et al. ....................... 502/162 |
| 5,055,552 | 10/1991 | Wong .................................. 502/162 |
| 5,091,507 | 2/1992 | Van Leeuwen et al. ........... 502/162 |
| 5,175,244 | 12/1992 | Budzelaar et al. ................. 502/162 |
| 5,229,343 | 7/1993 | Keijsper et al. ................... 502/162 |
| 5,247,065 | 9/1993 | van Doorn et al. ................ 502/162 |

FOREIGN PATENT DOCUMENTS 0121965 10/1984 European Pat. Off. .

*Primary Examiner*—Asok Pal
*Attorney, Agent, or Firm*—James O. Okorafor

[57] ABSTRACT

An improved process for the production of linear alternating polymers of carbon monoxide and at least one ethylenically unsaturated hydrocarbon employs a novel catalyst composition formed from a compound of palladium, the anion of a strong non-hydrohalogenic acid and a bidentate ligand of phosphorus wherein the divalent group bridging the two phosphorus atoms is 2-hydroxy-2-alkyl-1,3-propylene.

10 Claims, No Drawings

POLYMERIZATION PROCESS

This is a division of application Ser. No. 934,224, filed Aug. 25, 1992, now U.S. Pat. No. 5,247,065.

FIELD OF THE INVENTION

This invention relates to a process for the production of linear alternating polymers and to a novel catalyst composition useful in that process. More particularly, the invention relates to a process for the production of linear alternating polymers of carbon monoxide and at least one ethylenically unsaturated hydrocarbon.

BACKGROUND OF THE INVENTION

The class of linear alternating polymers of carbon monoxide and at least one ethylenically unsaturated hydrocarbon is now well known in the art. These materials, also known as polyketones or polyketone polymers, are represented by the repeating formula

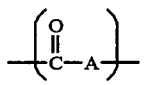 (I)

wherein A independently is a moiety derived from at least one ethylenically unsaturated hydrocarbon. The polyketone polymers are typically produced by contacting the carbon monoxide and hydrocarbon monomers under polymerization conditions in the presence of a reaction diluent and a catalyst composition formed from a compound of a Group VIII metal, the anion of a strong nonhydrohalogenic acid and a bidentate ligand of phosphorus, arsenic, antimony, nitrogen or sulfur. Without wishing to be limited, a preferred class of catalyst compositions is formed from a bidentate ligand of phosphorus wherein the divalent group bridging the two phosphorus atoms is linear and has three carbon atoms, i.e., the bridging group is 1,3-propylene (trimethylene).

The use of bidentate phosphine ligands containing a bridging group other than 1,3-propylene is known. The nature of catalyst compositions containing such substituted 1,3-propylene bridging groups has been examined, particularly when the bridging group is substituted on the central carbon atom. See, for example, U.S. Pat. No. 4,877,861 and U.S. Pat. No. 4,933,311 as well as copending U.S. patent application Ser. No. 684,109, filed Apr. 12, 1991. In general, the catalyst compositions formed from bidentate phosphine ligands containing 2-substituted-1,3-propylene bridging groups do not provide advantages over the ligands without substituents other than hydrogen in either or both of the two most important consideration for the polymerization process, i.e., faster reaction rate or high molecular weight polymer. It would be of advantage to have an improved process for the production of linear alternating polymers of carbon monoxide and at least one ethylenically unsaturated hydrocarbon which employs a bidentate phosphine ligand with a different type of substitution on the group bridging the two phosphorus atoms.

SUMMARY OF THE INVENTION

The present invention provides an improved process for the production of linear alternating polymers of carbon monoxide and at least one ethylenically unsaturated hydrocarbon, as well as a novel catalyst composition for use in the improved process. More particularly, the invention provides an improved process for the production of such polymers which employs a catalyst composition formed from a compound of palladium, the anion of strong nonhydrohalogenic acid and a bidentate phosphine ligand wherein the group bridging the two phosphorus atoms is a 2-hydroxy-2-alkyl-1,3-propylene group.

DESCRIPTION OF THE INVENTION

The polyketone polymers produced by the process of the invention are linear alternating polymers of carbon dioxide and at least one ethylenically unsaturated hydrocarbon. Suitable ethylenically unsaturated hydrocarbons for use as monomers in the process of the invention have up to 20 carbon atoms inclusive, preferably up to 10 carbon atoms inclusive, and are aliphatic including ethylene and other $\alpha$-olefins such as propylene, 1-butene, isobutylene, 1-hexene, 1-octene and 1-dodecene, or are arylaliphatic containing an aryl substituent on an otherwise aliphatic molecule, particularly an aryl substituent on a carbon atom of the ethylenic unsaturation. Illustrative of this latter class of ethylenically unsaturated hydrocarbons are styrene, p-methylstyrene, p-ethylstyrene and m-isopropylstyrene. The preferred polyketone polymers are copolymers of carbon monoxide and ethylene or terpolymers of carbon monoxide, ethylene and a second hydrocarbon of at least 3 carbon atoms, particularly an $\alpha$-olefin such as propylene.

When the preferred polyketone terpolymers are produced by the process of the invention there will be at least about two units incorporating a moiety of ethylene for each unit which incorporates a moiety of the second hydrocarbon. Preferably there will be from about 10 units incorporating a moiety of ethylene for each unit incorporating a moiety of the second hydrocarbon. The polymer chain of the preferred polyketone polymers is therefore represented by the repeating formula

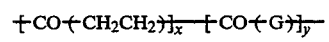 (II)

wherein G independently is a moiety derived from an ethylenically unsaturated hydrocarbon of at least 3 carbon atoms polymerized through the ethylenic unsaturation thereof, and the ratio of Y:X is no more than about 0.5. When copolymers are produced by the process of the invention there will be no second hydrocarbon present and the polymers are represented by the above formula II wherein Y is zero. When Y is other than zero, i.e., terpolymers are produced, the —CO—(—CH$_2$CH$_2$—)— units and the —CO—(—G—)— units are found randomly throughout the polymer chain and the preferred ratios of Y:X are from about 0.01 to about 0.1. The end groups or "caps" of the polymer chain will depend upon what materials were present during the polymerization and how and whether the polymer was purified. The precise nature of the end groups does not appear to influence the properties of the polymers to any considerable extent so that the polymers are fairly represented by the formula for the polymer chain as depicted above.

Of particular interest are the polyketone polymers of number average molecular weight from about 1000 to about 20,000, particularly those of number average molecular weight from about 20,000 to about 90,000, as determined by gel permeation chromatography. The physical properties of the polymer will depend in part upon the molecular weight, whether the polymer is a copolymer or a terpolymer and, in the case of terpolymers, the nature of and the proportion of the second hydrocarbon present. Typical melting points of the polymers are from 175° C. to about 300° C., more typically from about 210° C. to about 270° C. The polymers have a limiting viscosity number (LVN), as measured in m-cresol at 60° C. in a standard capillary viscosity measuring device, from about 0.5 dl/g to about 10 dl/g, more frequently from about 0.8 dl/g to about 4 dl/g.

The polyketone polymers are produced by contacting the carbon monoxide and hydrocarbon monomers under polymerization conditions in the presence of a reaction diluent and a catalyst composition formed from a compound of palladium, the anion of a strong non-hydrohalogenic acid and the particular bidentate ligand of phosphorus. The palladium compound is preferably a palladium carboxylate and palladiumacetate, palladium propionate, palladium hexanoate, and palladium octanoate are satisfactory. Palladium acetate is particularly preferred.

The strong non-hydrohalogenic acid is suitably an acid having a pKa below 2 (as measured in water at 18° C). Suitable acids are illustrated by inorganic acids such as sulfuric acid and perchloric acid, as well as by organic acids including carboxylic acids such as trifluoroacetic acid and difluoroacetic acid and trichloroacetic acid and sulfonic acids such as methanesulfonic acid, trifluoromethanesulfonic acid and p-toluenesulfonic acid. Anions of trifluoroacetic acid and p-toluenesulfonic acid are preferred. The anion is preferably provided as the free acid but alternatively the anion is provided as a salt, particularly the salt of a non-noble transition metal, e.g., a copper salt. However provided, the anion is present in a quantity from about 1 mol to about 100 mols per mol of palladium (as the salt). Preferred quantities of anion are from about 2 mols to about 50 mols of anion per mol of palladium.

The bidentate ligand of phosphorus is suitably represented by the formula

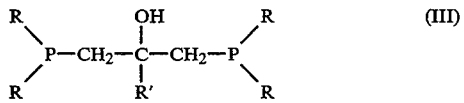

(III)

wherein R' is alkyl of up to 6 carbon atoms inclusive but preferably is methyl. The R group independently has up to 10 carbon atoms inclusive and is aliphatic or aromatic. R is suitably a hydrocarbyl group containing only atoms of carbon and hydrogen but also is suitably a substituted hydrocarbyl group containing other atoms in the form of chemically inert carbon atom substituents. Illustrative of aliphatic R groups are methyl, ethyl, propyl, hexyl, 2-chloroethyl and 3-dimethylaminopropyl. Hydrocarbyl aromatic groups are illustrated by phenyl, tolyl, and xylyl. The preferred R groups are phenyl or substituted hydrocarbyl aromatic groups, particularly those aromatic groups containing a polar substituent on at least one aromatic ring carbon atom ortho to the aromatic ring carbon atom through which the R group is attached to phosphorus. The preferred polar substituent of such aromatic groups is alkoxy, particularly methoxy, and these groups are illustrated by 2-methoxyphenyl, 2-ethoxyphenyl, 2,6-dimethoxyphenyl and 2-methoxy-6-ethoxy-4-propoxyphenyl. The particularly preferred R group is phenyl or 2-methoxyphenyl and the preferred bidentate phosphine ligands are 2-hydroxy-2-methyl-1,3bis(diphenylphosphino)propane and 2-hydroxy-2-methyl-1,3-bis[di(2methoxyphenyl)phosphino]propane. The ligand is employed in a quantity from about 0.5 mol to about 2 mols per mol of palladium. Preferred quantities of ligand are from about 0.75 mol to about 1.5 mol per mol of palladium.

The compounds of the above formula III are considered to be novel compounds and are produced by the reaction of an alkali metal phosphide of the formula $$R_2PM \qquad \text{(IV)}$$

wherein R has the previously stated significance, with a compound of the formula

(V)

$$X-CH_2-CR'OH-CH_2-R \qquad \text{(VI)}$$

wherein X is halo, e.g., chloro or bromo, preferably chloro, and R' has the previously stated significance. The preparation of the bidentate phosphine ligand takes place in an inert solvent such as liquid ammonia at reduced temperatures of about −80°. A reaction temperature of −78° C., the boiling point of liquid ammonia, is particularly useful.

It is useful on occasion to include within the catalyst composition solution an organic oxidizing agent. Suitable organic oxidizing agents include aliphatic nitrite compounds such as butyl nitrite or amyl nitrite, aromatic nitro compounds such as nitrobenzene and 2,4-dinitrotoluene. Preferred oxidizing agents, however, are the hydroquinones including both 1,4-hydroquinones and 1,2-hydroquinones. The 1,4-hydroquinones are particularly preferred, especially 1,4-benzoquinone. As stated, the presence of oxidizing agent is not required and amounts up to about 5000 mols of oxidizing agent per mol of palladium are useful. When present, quantities of oxidizing agent from about 10 mols to about 1000 mols per mol of palladium are preferred.

The contacting of monomeric reactants and catalyst composition is conducted in a suitable reactor under polymerization conditions in the presence of a reaction diluent. Suitable diluents include alkanols such as methanol or ethanol and alkanones such as acetone or methyl ethyl ketone. Methanol is the preferred reaction diluent. The polymerization conditions include a reaction temperature of from about 25° C. to about 150° C. Temperatures from about 30° C. to about 130° C. are preferred. The reaction pressures from about 2 bar to about 150° C. are satisfactory with pressures from about 5 bar to about 100 bar being more frequently encountered.

The reactant/catalyst composition is facilitated by some means of agitation such as shaking or stirring. The molar ratio of carbon monoxide to total ethylenically unsaturated hydrocarbon is from about 10:1 to about 1:5. Sufficient catalyst composition is employed to provide from about $1\times10^{-7}$ mol to about $1\times10^{-3}$ mol of palladium per mol of total ethylenically unsaturated hydrocarbon. Preferred quantities of catalyst composition provide from about $1\times10^{-6}$ mol to about $1\times10^{-4}$ mol of palladium per mol of total ethylenically unsaturated hydrocarbon. Subsequent to polymerization, the reaction is terminated as by cooling the reaction mixture and releasing the pressure. The polyketone polymer is typically obtained as a suspension in the reaction diluent and is recovered by conventional methods such as filtration or decantation. The polyketone is used as recovered or is purified as by contacting with a solvent or extraction agent which is selective for catalyst residue.

The polyketone polymers are premium thermoplastic polymers of established utility. They are processed by methods conventional for thermoplastics such as extrusion, injection molding or thermoforming into a variety of shaped articles. specific application include the production of containers for food and drink and parts and housings for automotive applications.

The invention is further illustrated by the following Comparative Examples (not of the invention) and the Illustrative Embodiments which should not be regarded as limiting. In the Comparative Examples and Illustrative Embodiments all copolymers of carbon monoxide and ethylene were examined by NMR analysis and found to be linear with units derived from carbon monoxide alternating with unites derived from ethylene. In the terpolymers of carbon monoxide, ethylene and propylene, the terpolymers were found to be linear with units derived from carbon monoxide alternating with randomly ordered units derived from ethylene or propylene. All LVN values were determined with a capillary viscosity measuring device in m-cresol at 60° C.

ILLUSTRATIVE EMBODIMENT I

The compound 2-hydroxy-2-methyl-1,3-bis(diphenylphosphino)propane was prepared by adding 22.8 g (86.95 mmol) triphenylphosphine to a solution of 4.0 g (174 mmol) sodium in 400 ml liquid ammonia, which solution was maintained a −78° C. The resulting mixture was stirred for 45 minutes while maintained at −78° C. and 4.2 g (78.5 mmol) ammonium chloride was added. After an additional 30 minutes, a solution of 4.63 g (43.5 mmol) of 1-chloro-2,3-epoxy-2-methylpropane in 150 ml tetrahydrofuran was added. After evaporation of ammonia, the solvent was removed under reduced pressure and water and dichloromethane were added to the residue. The organic layer was separated and filtered. After removal of the dichloromethane, the solid residue was washed with n-hexene. The yield of the novel 2-hydroxy-2-methyl-1,3-bis(diphenylphosphino)propane was 14 g (73%).

COMPARATIVE EXAMPLE I

The compound 2-hydroxy-2-phenyl-1,3-bis(diphenylphosphino)propane was prepared by a procedure similar to that of Illustrative Embodiment I. To a solution of 4.2 g (183 mmol sodium maintained in liquid ammonia at −78° C. was added 23.95 g (91.95 mmol) triphenylphosphine. After 45 minutes of stirring the resulting mixture at −78° C., 2.14 g (40 mmol) ammonium chloride was added. After an additional 30 minutes a solution of 9.23 g (45 mmol) of 1,3-dichloro-2-hydroxy-2-phenyl propane in 150 ml ether was added. After evaporation of ammonia, the product was recovered by the procedure of Illustrative Embodiment I. The yield of novel 2-hydroxy-2-phenyl-1,3-bis(diphenylphosphino)propane was 15 g (68%).

COMPARATIVE EXAMPLE II

A copolymer of carbon monoxide and ethylene was produced by charging 200 ml of methanol to an autoclave of 300 ml capacity equipped with a mechanical stirrer. The air present in the autoclave was expelled by thrice charging carbon dioxide to the autoclave to a pressure of 50 bar and then releasing the pressure. After the autoclave contents had been warmed to 65° C., a equimolar mixture of carbon dioxide and ethylene was charged to the autoclave until a pressure of 55 bar had been reached. A catalyst composition solution was then added which comprised 6 ml methanol, 0.02 mmol palladium acetate, 0.04 mmol p-toulenesulfonic acid, and 0.02 mmol 1,3-bis(diphenylphosphino)propane. During the resulting polymerization the equimolar mixture was added to maintain a constant pressure. After 3 hours, the polymerization was terminated by cooling the autoclave and contents to room temperature and releasing the pressure. The polymer product was recovered by filtration, washed with methanol and dried. The copolymer had an LVN of 1.2 dl/g and had been produced at the rate of 1.3 kg of copolymer/g Pd hr.

COMPARATIVE EXAMPLE III

A carbon monoxide/ethylene copolymer was produced by a procedure substantially similar to that of comparative Example II except that a polymerization temperature of 85° C. instead of 65° C. was used. The copolymer had an LVN of 0.6 dl/g and had been produced at the rate of 5.0 kg of copolymer/g Pd hr.

COMPARATIVE EXAMPLE IV

A copolymer of carbon monoxide and ethylene was produced by a procedure substantially similar to that of Comparative Example II except that 0.02 mmol 2-(diphenylphosphinomethyl)-3-(diphenyl-phosphino)propane-1 was used instead of 1,3-bis(diphenylphosphino)propane and the reaction temperature was 85° C. instead of 65° C. The copolymer product had an LVN of 0.6 dl/g and was produced at the rate of 5.4 kg of copolymer/g Pd hr.

COMPARATIVE EXAMPLE V

A copolymer of carbon monoxide and ethylene was produced by charging 200 ml of methanol to an autoclave of 300 ml capacity equipped with a mechanical stirrer. After the contents of this autoclave had been warmed to 85° C., a equimolar mixture of carbon monoxide and ethylene was added until a pressure of 55 bar had been reached. A catalyst composition solution was then added which comprised 6 ml methanol, 0.01 mmol palladium acetate, 0.02 mmol trifluoroacetic acid and 0.01 mmol 1,3-bis(diphenylphosphino)propane. During the resulting polymerization the pressure was maintained by adding additional equimolar mixture. After 5 hours, the polymerization was terminated by cooling the autoclave and contents to room temperature and releasing the pressure. The polymer product was recovered by filtration, washed with methanol and dried. The copolymer product had an LVN of 1.0 dl/g and was produced at a rate of 5.6 kg of copolymer/g Pd hr.

COMPARATIVE EXAMPLE VI

A carbon monoxide/ethylene copolymer was produced by a procedure substantially similar to Comparative Example V except that the catalyst composition solution contained 0.02 mmol p-toluenesulfonic acid instead of trifluoroacetic acid and 0.01 mmol 2-methyl-2-(diphenylphosphinomethyl)-1,3-bis(diphenylphosphinomethyl)-1,3-bis(diphenylphosphino)propane instead of 1,3-bis-(diphenylphosphino)propane. The copolymer product had an LVN of 0.7 dl/g and was produced at a rate of 4.7 g of copolymer/g Pd hr.

COMPARATIVE EXAMPLE VII

A terpolymer of carbon monoxide, ethylene and propylene was produced by charging, into an autoclave of 300 ml capacity equipped with a mechanical stirrer, a catalyst composition comprising 135 ml methanol, 4 ml acetone, 0.009 mmol palladium acetate, 0.19 mmol trifluoroacetic acid and 0.01 mmol 1,3-bis(diphenylphosphino)propane. The air present was expelled by thrice pressurizing the autoclave to 50 bar with carbon monoxide and releasing the pressure. The contents of the autoclave were warmed to 80° C. and carbon monoxide was added until a pressure of 25 bar had been reached. Propylene was then added until a pressure of 35 bar had been reached and then ethylene was added to obtain a total pressure of 50 bar. During the resulting polymerization the pressure within the autoclave was maintained by adding an equimolar mixture of carbon monoxide and ethylene. After 3.1 hours the polymerization was terminated by cooling the reactor and contents to room temperature and releasing the pressure. The terpolymer product was recovered by filtration, washed with methanol and dried. The terpolymer had an LVN of 0.5 dl/g and the polymer was produced at the rate of 4.4 kg of terpolymer/g Pd hr.

COMPARATIVE EXAMPLE VIII

A terpolymer of carbon monoxide, ethylene and propylene was produced by a procedure substantially similar to that of Comparative Example VII except that the catalyst composition contained 0.01 mmol 2-benzyloxy-1,3-bis(diphenyl-phosphino)propane instead of 1,3-bis(diphenylphosphino)propane, the reaction temperature was 85° C. instead of 80° C. and the reaction time was 2.7 hours instead of 3.1 hours. The terpolymer product had an LVN of 0.3 dl/g and was produced at the rate of 3.0 kg of terpolymer/g Pd hr.

COMPARATIVE EXAMPLE IX

A carbon monoxide/ethylene copolymer was prepared by charging 133 ml of methanol to an autoclave of 266 ml capacity equipped with a mechanical stirrer. The air present in the autoclave was expelled by thrice pressurizing the autoclave with carbon monoxide to 50 bar and then releasing the pressure. A catalyst composition solution was then introduced into the autoclave which comprised 7 ml acetone, 0.017 mmol palladium acetate, 0.036 mmol p-toluenesulfonic acid and 0.018 mmol 1,3-bis(diphenylphosphino)propane. After the contents of the autoclave had been warmed to 85° C., an equimolar mixture of carbon monoxide and ethylene was added until a pressure of 55 bar was reached. During the resulting polymerization, the pressure was maintained by adding additional equimolar mixture. After 1.75 hours the polymerization was terminated by cooling the autoclave and contents to room temperature and releasing the pressure. The polymer was recovered by filtration, washed with methanol and dried. The copolymer product had an LVN of 0.9 dl/g and was produced at the rate of 3.7 kg of copolymer/g Pd hr.

ILLUSTRATIVE EMBODIMENT II

A carbon monoxide/ethylene copolymer was prepared by a procedure substantially similar to that of Comparative Example IX except that the catalyst composition solution contained 0.016 mmol palladium acetate instead of 0.017 mmol and 0.018 2-hydroxy-2-methyl-1,3-bis(diphenylphosphino)propane, and the reaction time was 1.23 hour instead of 1.75 hour. The copolymer product had an LVN of 1.0 dl/g and was prepared at the rate of 5.6 kg/g Pd hr.

COMPARATIVE EXAMPLE X

A copolymer of carbon monoxide and ethylene was produced by a procedure substantially similar to that of Comparative Example IX except that the catalyst composition solution contained 0.016 mmol palladium acetate instead of 0.017 mmol, 0.035 mmol of p-toluenesulfonic acid instead of 0.036 mmol, 0.019 mmol 2-hydroxy-2-phenyl-1,3-bis(diphenylphosphino)propane instead of 1,3-bis(diphenylphosphino)propane and the reaction time was 1.23 hours instead of 1.75 hours. The copolymer product had an LVN of 1.0 dl/g and was produced at the rate of 2.6 kg of copolymer/g Pd hr.

What is claimed is:

1. A catalyst composition formed from a compound of palladium, the anion of a non-hydrohalogenic acid having a pKa below 2 and a bidentate ligand of phosphorus wherein the divalent group bridging the two phosphorus atoms is 2-hydroxy-2-alkyl-1,3propylene.

2. The catalyst composition of claim 1 wherein the bidentate ligand is of the formula

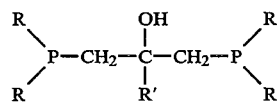

wherein R independently is aliphatic or aromatic of up to 10 carbon atoms inclusive and R' is alkyl of up to 6 carbon atoms inclusive.

3. The catalyst composition of claim 2 wherein the compound of palladium is a palladium carboxylate.

4. The catalyst composition of claim 3 wherein the anion is the anion of trifluoroacetic acid or p-toluenesulfonic acid.

5. The catalyst composition of claim 4 wherein R independently is phenyl or substituted aromatic hydrocarbyl having a polar substituent on at least one aromatic ring carbon atoms ortho to the aromatic ring carbon atom through which the R group is attached to the phosphorus.

6. The catalyst composition of claim 5 wherein the palladium carboxylate is palladium acetate.

7. The catalyst composition of claim 6 wherein R is 2-methoxyphenyl.

8. The catalyst composition of claim 6 wherein R is phenyl.

9. The catalyst composition of claim 8 wherein the anion is the anion of trifluoroacetic acid.

10. The catalyst composition of claim 8 wherein the anion is the anion of p-toluenesulfonic acid.

* * * * *